US006902554B2

(12) United States Patent
Huttner

(10) Patent No.: US 6,902,554 B2
(45) Date of Patent: Jun. 7, 2005

(54) METHOD FOR CONTROLLING THE PAIN FROM INJECTIONS OR MINOR SURGICAL PROCEDURES AND APPARATUS FOR USE THEREWITH

(75) Inventor: James J. Huttner, Sylvania, OH (US)

(73) Assignee: Bionix Development Corporation, Toledo, OH (US)

( * ) Notice: Subject to any disclaimer, the term of this patent is extended or adjusted under 35 U.S.C. 154(b) by 356 days.

(21) Appl. No.: 09/919,202

(22) Filed: Jul. 31, 2001

(65) Prior Publication Data

US 2002/0013602 A1 Jan. 31, 2002

Related U.S. Application Data

(60) Provisional application No. 60/221,906, filed on Jul. 31, 2000, and provisional application No. 60/259,788, filed on Jan. 4, 2001.

(51) Int. Cl.[7] .............................................. A61M 31/00
(52) U.S. Cl. ...................................... 604/500; 604/116
(58) Field of Search ........................ 604/112, 115–117, 604/500, 506, 174, 179, 180, 187; 606/201, 204

(56) References Cited

U.S. PATENT DOCUMENTS

| 3,620,209 A | * 11/1971 | Kravitz .......................... 601/79 |
| 5,364,362 A | 11/1994 | Schulz |

OTHER PUBLICATIONS

Davis, Peter; Opening Up the Gate Control Theory; Nurs Stand, Jul. 28–Aug. 3, 1993; 7(45):25–7.
Apkarian, et al.; Heat–Induced Pain Diminishes Vibrotactile Perception: A Touch Gate; Somatosens Mot. Res. 1994; 11 (3): 259–67.

Melzack, Ronald; From the Gate to the Neuromatrix; Pain Supplement 6 (1999) S121–S126; Published by Elsevier Science B.V.

Barnhill, et al.; Using Pressure to Decrease the Pain of Intramuscular Injections; Journal of Pain and Symptom Management, vol. No. 12, Jul. 1996 ppgs. 52–58; Published by Elevier, New York, New York.

* cited by examiner

*Primary Examiner*—LoAn H. Thanh
(74) *Attorney, Agent, or Firm*—Marshall & Melhorn, LLC

(57) ABSTRACT

The pain associated with an injection or minor surgical procedure at a site on the skin of a patient is reduced by urging a skin engaging surface of a pressure member against the skin proximate the site, thereby stimulating the large diameter afferent sensory nerve fibers in the skin proximate the site and at least partially blocking pain signals from the small diameter afferent pain nerve fibers in the skin proximate the site. An apparatus for use in this method comprises a pressure member having a skin engaging surface adapted to be pressed against the skin of a patient proximate the site to stimulate the large diameter afferent sensory nerve fibers in the skin proximate the site. In certain embodiments, the skin engaging surface is comprised of a plurality of projections extending from the pressure member. Various embodiments include a syringe retainer adapted to be secured to a syringe, and a least one resilient member, such as a spring, resiliently securing the pressure member to the syringe retainer.

13 Claims, 5 Drawing Sheets

METHOD FOR CONTROLLING THE PAIN FROM INJECTIONS OR MINOR SURGICAL PROCEDURES AND APPARATUS FOR USE THEREWITH

RELATED APPLICATIONS

This application is claiming the benefit, under 35 U.S.C. § 119(e), of the provisional application filed Jul. 31, 2000 under 35 U.S.C. § 111(b), which was granted Ser. No. 60/221,906, and the provisional application filed Jan. 4, 2001 under 35 U.S.C. § 111(b), which was granted Ser. No. 60/259,788. Both provisional applications are hereby incorporated by reference.

BACKGROUND OF THE INVENTION

The invention relates to a method of reducing or eliminating the pain from injections or minor surgical procedures by the local application of pressure about the injection or surgical site to block afferent pain fiber transmission. The invention further relates to devices that can be used to apply local pressure to an injection or surgical site to reduce or eliminate the pain associated therewith.

The pain elicited by administering minor injections, such as those with childhood immunizations, is a significant cause of stress in the medical office. It causes fear and anxiety in patients both young and old. It can create difficulties in developing patient rapport and confidence, and can even impair the physician's ability to perform an examination because of a patient's overriding preoccupation with the forthcoming shot or procedure. Any procedure and/or device that diminishes the pain associated with simple injections or minor surgical procedures would be of great help.

Such a procedure and/or device could be especially useful, as another example, to those with diabetes. Diabetes is a common disorder of the endocrine system affecting millions of individuals worldwide. In diabetes, the body loses its ability to manufacture insulin, a hormone produced normally in the islets cells of the pancreas. Insulin has many functions, but its primary function is to promote glucose uptake from the blood into the cells of the body where it can be metabolized to provide energy for those cells. In diabetes, the lack of insulin causes blood sugar to rise to dangerously high levels, causing dehydration and possible brain injury. At the same time, cells starved for glucose turn to fat metabolism for energy production, causing ketonemia and life threatening acidosis.

This severe disruption of the body's physiology and many of the later sequellae of diabetes can be avoided by giving insulin to diabetic patients. However, because insulin is a protein, the only currently available forms of the hormone must be given via injection. The sites chosen are usually the thigh and the abdomen, and diabetic patients often must take multiple injections of insulin daily. Newer treatment protocols advocate even tighter control involving six or more injections daily.

The pain elicited by chronic insulin injections is a constant source of anxiety and stress to the diabetic patient. Even when resigned to a lifetime of insulin injections, the pain associated with daily insulin shots is never appreciated. In fact, in some cases such pain can keep the diabetic patient from following a more aggressive insulin protocol just so he/she can avoid the increased number of injections. It will be appreciated that any device and/or procedure that diminishes the pain associated with daily insulin injections would be of great help.

Current studies have supported the gate control theory of pain awareness and transmission. Briefly stated, pain is elicited when noxious stimuli trigger nociceptive nerve endings in the skin. Pain impulses are then transmitted by small diameter peripheral afferent fibers through the spinal cord to the brain. Gate theory states that there is a gating mechanism in the dorsal horn of the spinal cord that acts to facilitate or inhibit transmission of pain signals to the brain. Stimulation of the small diameter nociceptive (pain) fibers opens the gate. The gate can be closed by simultaneous stimulation of large diameter afferent sensory nerve fibers, such as those that respond to mechanical stimuli such as touch and vibration.

Although gate control theory probably oversimplifies the true complexity of the body's regulation of pain, it has proved to be a useful guide to understanding and predicting pain and its control. Practical application of gate control theory has led to the development and widespread use of TENS units. TENS, transcutaneous electrical nerve stimulation, stimulates large diameter afferent sensory fibers with repetitive electrical impulses to use gate control to block pain signals from small diameter afferent pain nerve fibers. In many individuals with chronic pain TENS units employing the gate control theory of pain management provide significant and predictable relief from their pain.

Anecdotal experience by physicians has shown that the local application of pressure can reduce the pain from simple injections. A recent study was performed that documented and quantified this ability of simple applied finger pressure to reduce needle pain. These findings, reported in the *Journal of Pain and Symptom Management*, Vol. 12, No. 1, July 1996, pp. 52–58, support gate control theory and provide evidence that mechanical pressure can directly affect a person's sensation of pain.

SUMMARY OF THE INVENTION

The invention is directed to a method of reducing or eliminating the pain from injections or minor surgical procedures by the local application of pressure about the injection or surgical site to block afferent pain fiber transmission. Such minor surgical procedures might include, as examples, small shave or punch biopsies, the freezing of warts, and procedures involving needle electrodes. The invention further relates to devices that can be used to apply local pressure to an injection or surgical site to reduce or eliminate the pain associated therewith.

The method of the invention reduces the pain associated with penetration of the skin of a patient at a site with a needle or surgical instrument by urging a skin engaging surface of a pressure member against the skin of a patient at the site. This stimulates the large diameter afferent sensory nerve fibers in the skin proximate the site and at least partially blocks pain signals from the small diameter afferent pain nerve fibers in the same area. By penetration of the skin, as used herein, it is meant penetration of at least an outer layer of the skin by a needle or surgical instrument.

An apparatus in accordance with the invention comprises a pressure member having a skin engaging surface adapted to be pressed against the skin of a patient at the site to stimulate the large diameter afferent sensory nerve fibers in the skin proximate the site and at least partially block pain signals from the small diameter afferent pain nerve fibers in the skin proximate that site. In certain embodiments of the invention, the skin engaging surface is comprised of a plurality of projections extending from the pressure member. It is believed that such a plurality of projections promotes blocking of pain signals from the small diameter afferent pain nerve fibers in the skin proximate the site.

The pressure member of the apparatus of the invention may have an aperture about which the skin engaging surface extends. Such an aperture is aligned with the injection or surgical site, and the needle or surgical instrument is introduced through the aperture to penetrate the skin. Such a structure permits the skin engaging surface of the pressure member to substantially surround the site in a manner believed to promote the blocking of pain signals from the small diameter afferent pain nerve fibers in the skin proximate the site.

In various embodiments of the invention, an apparatus for reducing the pain associated with the penetration of the skin of a patient at a site with a needle or surgical instrument is provided that comprises a pressure member having a slot adapted to receive the needle or surgical instrument. Such a slot may be aligned, for example, with a patient's blood vessel during a procedure to draw blood from the patient or for the insertion of an IV catheter. In such cases, the slot may extend to the perimeter of the pressure member, so that the pressure member does not occlude the vessel ahead of the site of the procedure.

In other embodiments related to the use of the invention specifically with injections from a hypodermic needle, the apparatus of the invention is comprised of a pressure member having a skin engaging surface and a syringe retainer adapted to be secured to a syringe. At least one spring resiliently secures the pressure member to the syringe retainer. The spring is adapted to be compressed under the force used to administer an injection to a patient, allowing a reduction in the distance between the pressure member and the syringe retainer so that the needle can penetrate the skin at the site.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE PREFERRED EMBODIMENTS

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

Figure 1:
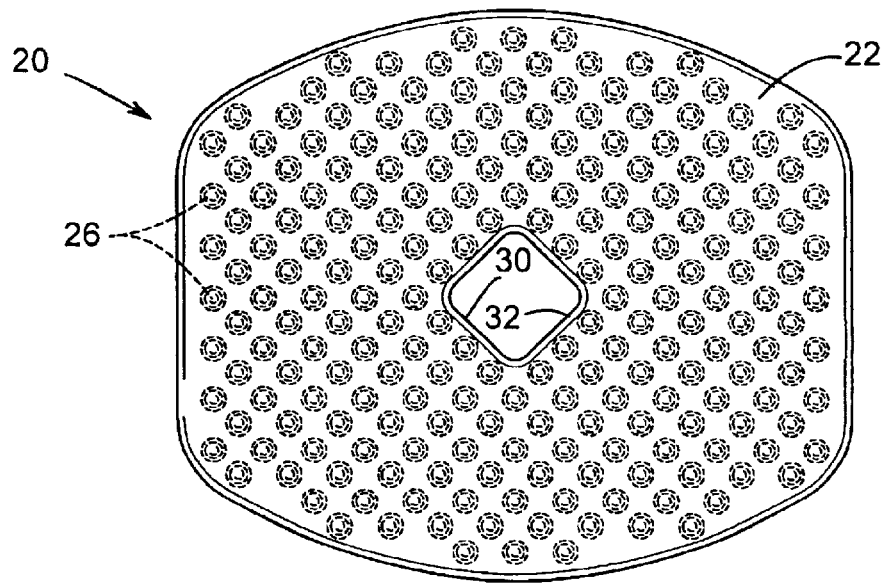
FIG. 1 is a top view of a first embodiment of an apparatus in accordance with the invention with features on the underside shown in hidden lines.
Figure 2:
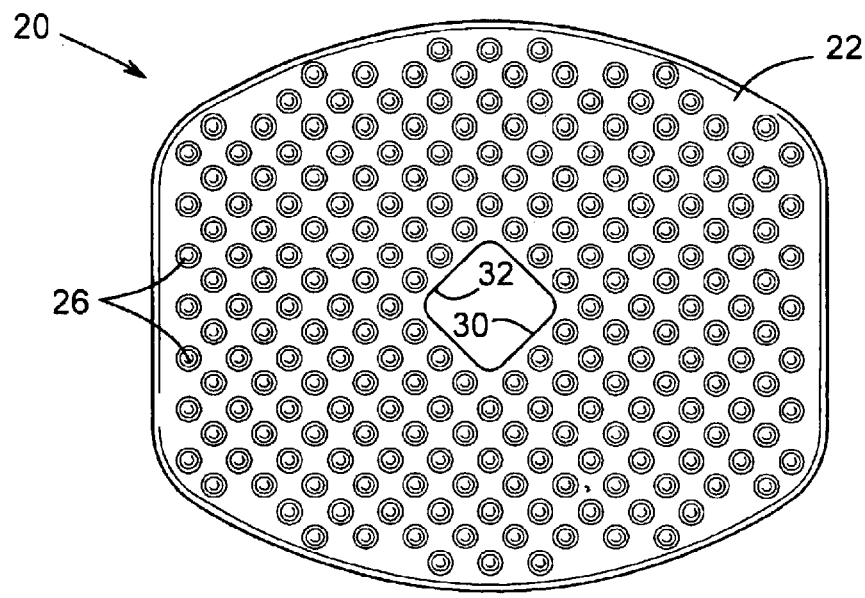
FIG. 2 is a bottom view of the apparatus of FIG. 1.
Figure 3:
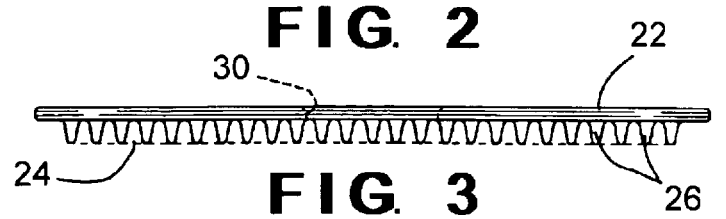
FIG. 3 is a side view of the apparatus of FIG. 1.
Figure 4:
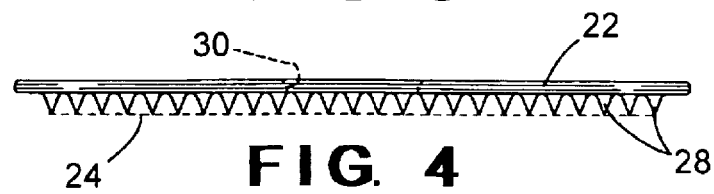
FIG. 4 is a side view of a second embodiment of the apparatus.

Referring now to the drawings, FIGS. 1 through 3 show a first embodiment of an apparatus in accordance with the invention for reducing or eliminating the pain from injections or minor surgical procedures by the local application of pressure about the injection or surgical site to block afferent pain fiber transmission. The apparatus, denoted generally as 20 in the drawing, includes a pressure member 22. As illustrated in FIG. 3, the pressure member 22 is a relatively thin, generally flat disk that has a skin engaging surface 24 on its underside. In this first embodiment, the skin engaging surface 24 is formed by the ends of a plurality of projections 26 that are spaced about and extend from the underside of the pressure member 22. The projections 26 in this embodiment are substantially frustoconical in shape, with rounded ends. FIG. 4 illustrates an embodiment of the apparatus identical to that shown in FIGS. 1–3, except that the projections 28 have a less blunt, conical shape.

It will be understood that in practice projections having a number of shapes and configurations will provide adequate sensory and pressure nerve stimulation and thus will be efficacious in this application and may be substituted for the substantially conical and frustoconical shapes illustrated. In general, it will be preferred that the ends of the projections be blunt relative to the end of the needle or surgical instrument being used.

An aperture 30 is provided in the pressure member 22 to allow a nurse or physician to administer the injection or access the surgical site once the device has been applied to the skin. As shown in FIGS. 1–4, the aperture 30 is generally centrally located. Such a configuration allows the aperture 30, and thus the injection or surgical site, to be substantially surrounded by the projections 26. The aperture 30 should be of a size sufficient to allow the nurse or physician to administer injections or perform minor surgical procedures and may, of course, be of various sizes and shapes depending upon the procedure being performed. The upper peripheral edge 32 of the aperture 30 may be chamfered or beveled towards the patient so as to promote access for administering sub-cutaneous injections, which are administered at an angle into the upper layers of the skin.

As an alternative to providing an aperture, the pressure member in the various embodiments of the invention could be formed out of material, such as a silicone rubber sheet, that allows a needle to pass through at any point, obviating the need for an opening. Finger needle guards (not shown) could also be provided for extra operator safety.

The peripheral edge 34 of the pressure member 22 may be configured, as illustrated in FIGS. 1 and 2, so as to have at least one noncircular section to facilitate handling of the pressure member. The apparatus 20 might also be equipped with finger grips (not shown) on its upper surface to enable a nurse or physician to firmly grasp the device by means of such grips.

The apparatus of the invention, in its various embodiments, may be formed of any suitable material or combination of materials. The material forming the pressure member is preferably flexible enough to substantially conform to the contours of the skin in the vicinity of the injection or surgical site as the pressure member is forced against the skin. This allows for the application of a greater number of the projections to the skin of the patient proximate the site. The material forming the pressure member and projections is preferably sufficiently stiff that relatively equal pressure is provided to the skin from the plurality of projections. Polymeric materials such as polyethylene are suitable. The entire apparatus may be molded as an integral part from a polymeric material such as polyethylene. In certain applications, it may be an advantage to form the pressure member of a relatively stiff material, such as a rigid metal.

Figure 5:
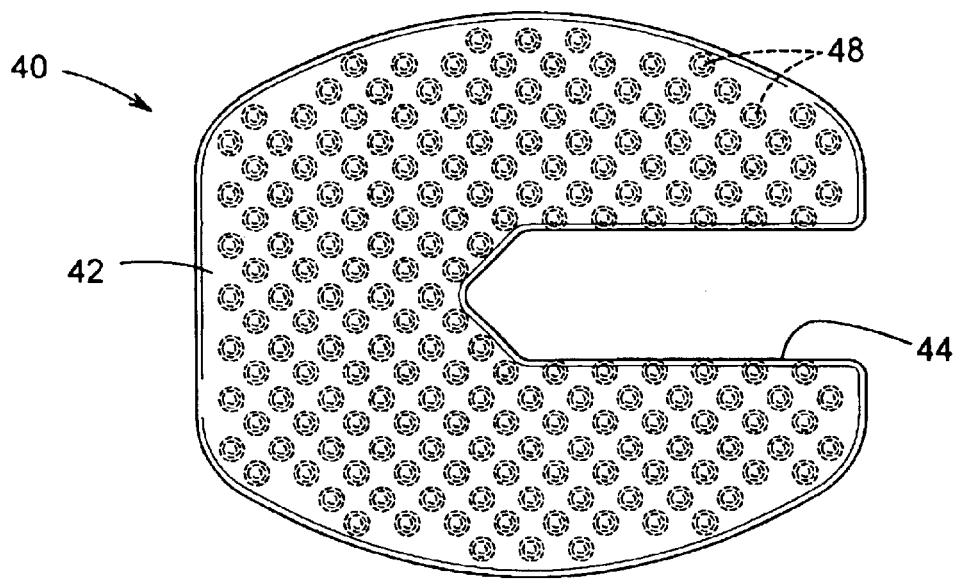
FIG. 5 is a top view of a third embodiment of an apparatus in accordance with the invention with features on the underside shown in hidden lines.
Figure 6:
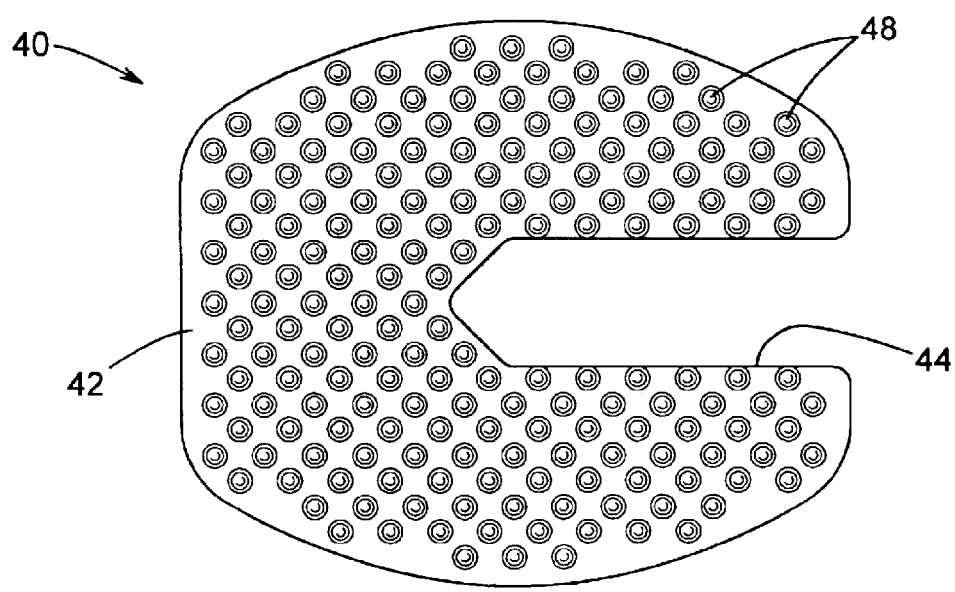
FIG. 6 is a bottom view of the apparatus of FIG. 5.
Figure 7:
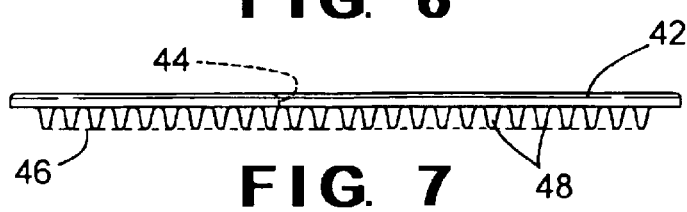
FIG. 7 is a side view of the apparatus of FIG. 5.

FIGS. 5–7 illustrate another embodiment of the apparatus of the invention. In this embodiment, the apparatus 40 includes a pressure member 42 having a slot 44 formed therein. The slot 44 extends from a generally central portion of the pressure member 42 radially outward, defining a gap in the peripheral edge 46 of the pressure member 42. The pressure member 42 of this embodiment is thus of a generally U-shaped configuration. The slot 44 is adapted to be aligned with a portion of a blood vessel of the patient proximate a site intended, for example, for drawing blood or the placement of an IV catheter. This would prevent the apparatus 40 from occluding both ends of a blood vessel and allow the device to be used to place IV catheters, draw blood or the like.

As illustrated in FIG. 5, the pressure member 42 is a relatively thin, generally flat disk that has a skin engaging surface 46 on its underside. In this embodiment, the skin engaging surface 46 is formed by the ends of a plurality of projections 48 that are spaced about and extend from the underside of the pressure member 42. The projections 48 in this embodiment are substantially frustoconical in shape, with rounded ends.

Figure 8:
FIG. 8 is a side view of a fourth embodiment of the apparatus.

FIG. 8 illustrates a further embodiment of the apparatus, identical to that shown in FIGS. 5–7, except that the projections 50 have a less blunt, conical shape. Again, projections having a number of shapes and configurations will provide adequate sensory and pressure nerve stimulation and thus will be efficacious in this application.

FIG. 6 illustrates another embodiment of an apparatus 52 in accordance with the invention. In this embodiment, the pressure member 54 is a relatively thin, generally flat disk that has a skin engaging surface defined on its underside by the ends of a plurality of projections 56 that are spaced about and extend from the pressure member 54. As illustrated, the projections 56 are substantially conical in shape, although other shapes and configurations can also be employed.

Figure 9:
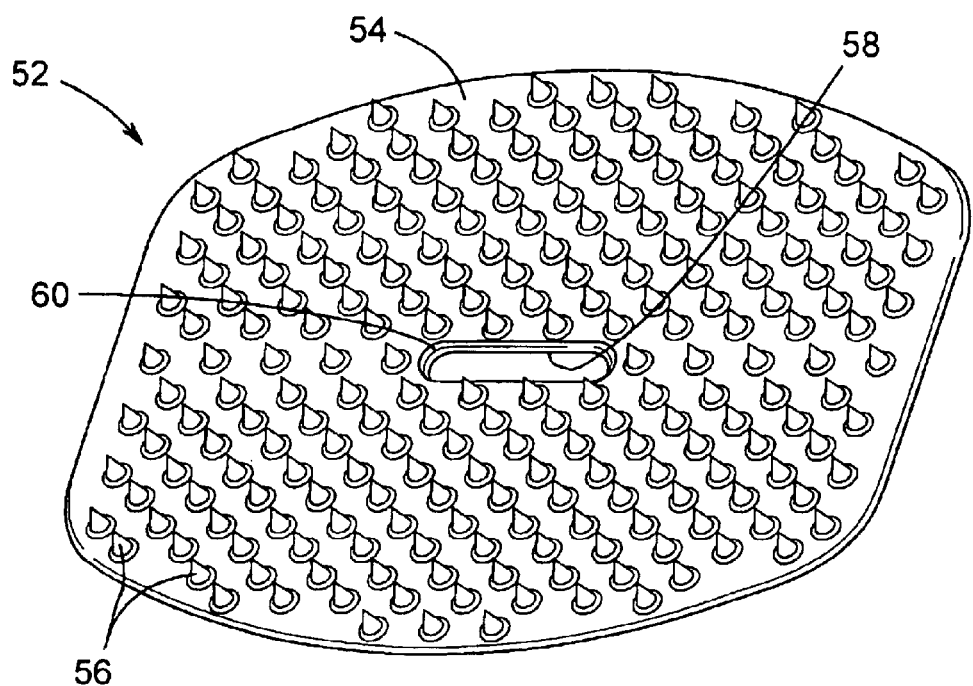
FIG. 9 is a perspective view of a fifth embodiment of an apparatus in accordance with the invention.

An aperture 58 is provided in the pressure member 54 to allow for the administration of an injection or to allow access the surgical site once the apparatus 52 has been applied to the skin of a patient. As shown in FIG. 9, the aperture 58 is formed as an elongate slot that is generally centrally located in the pressure member 54. The upper peripheral edge 60 of the aperture 58 is chamfered.

Figure 10:
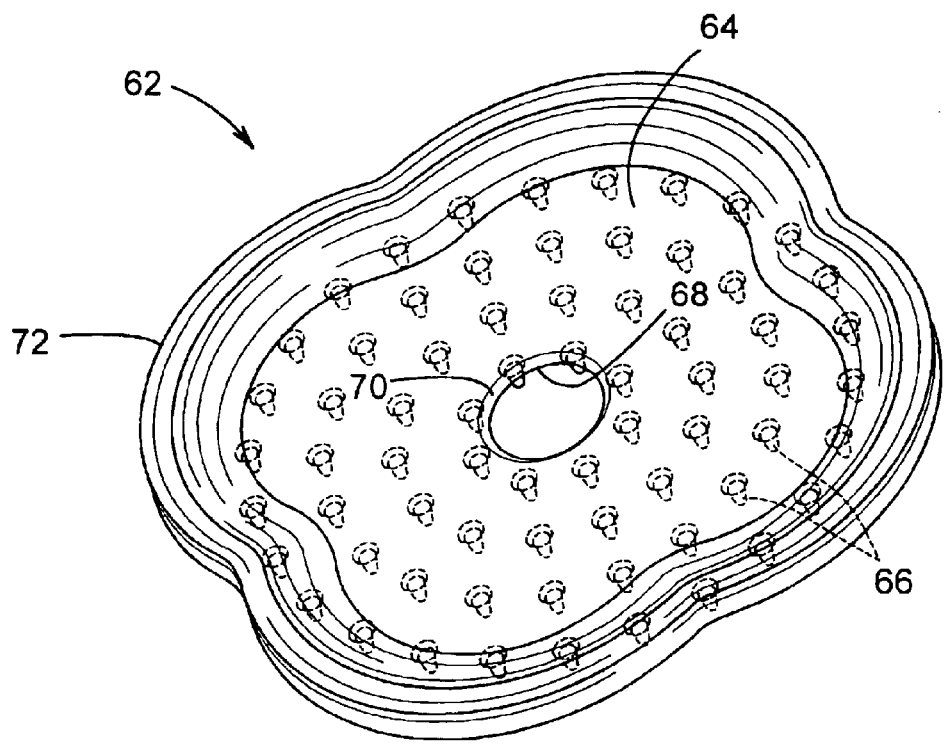
FIG. 10 is perspective view of a sixth embodiment of an apparatus in accordance with the invention with features on the underside shown in hidden lines.

The embodiment 62 shown in FIG. 10 includes a pressure member 64. As illustrated in FIG. 3, the pressure member 64 is a relatively thin, generally flat disk that has a skin engaging surface on its underside formed by the ends of a plurality of projections 66. The projections 66 extend from the underside of the pressure member 64 and are spaced about and surround a generally centrally located aperture 68. Again, the upper peripheral edge 70 of the aperture 68 may be chamfered so as to promote access for administering injections at an angle to the skin.

The peripheral edge 72 of the pressure member 64 may be configured so as to have at least one noncircular section to facilitate handling of the pressure member. In the embodiment of FIG. 10, the peripheral edge 72 is scalloped, giving the apparatus a generally cloverleaf shape. The peripheral edge 72 may also be formed with a greater thickness than the thickness of the more central portions of the pressure member 64, thereby defining a raised lip about the periphery of the pressure member 64.

Figure 11:
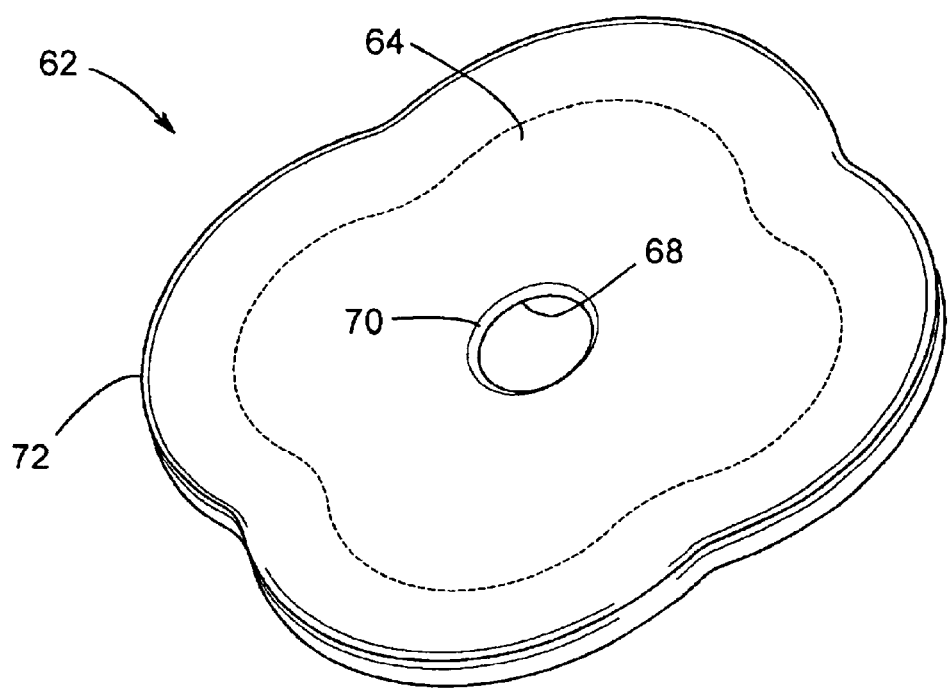
FIG. 11 is perspective view of a seventh embodiment of an apparatus in accordance with the invention with features on the underside shown in hidden lines.

FIG. 11 illustrates an embodiment that is identical to that shown in FIG. 10 except for the skin engaging surface. In this embodiment, the skin engaging surface on the underside of the pressure member 64 is a relatively smooth, continuous surface except for the aperture 68. It believed that, while the apparatus of this embodiment will reduce the pain associated with penetration of the skin of a patient at a site with a needle or surgical instrument when utilized in accordance with the method of the invention, it will not be as effective in doing so as the alternate embodiments shown herein.

Figure 12:
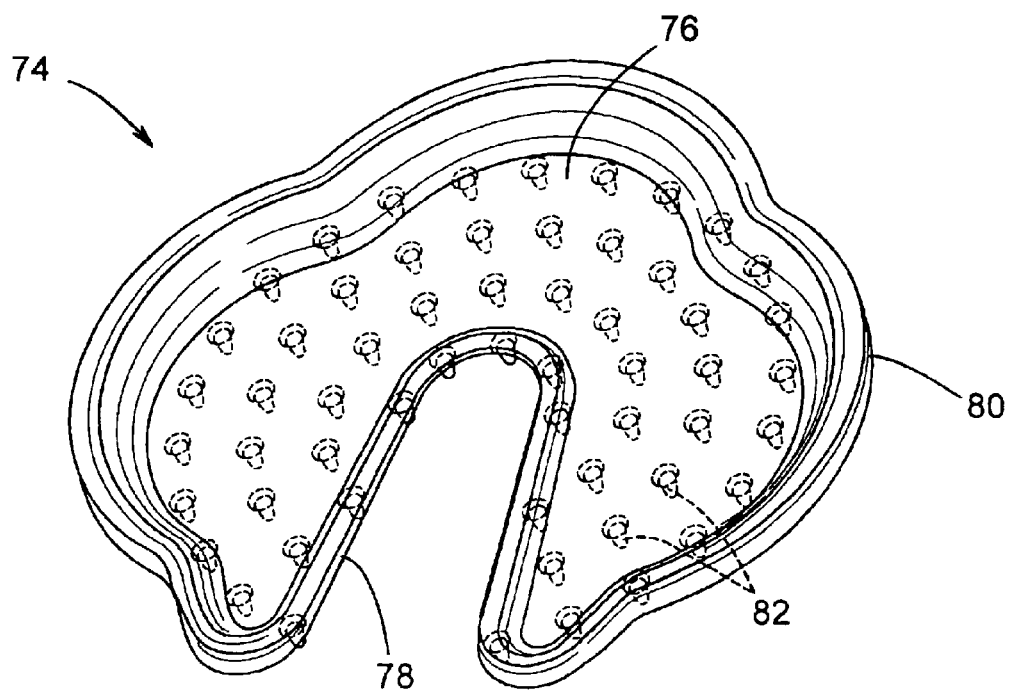
FIG. 12 is perspective view of an eighth embodiment of an apparatus in accordance with the invention with features on the underside shown in hidden lines.

FIG. 12 shows a further embodiment that is identical to that shown in FIG. 10 except for the aperture formed in the pressure member. In this embodiment, in which the apparatus is denoted generally as numeral 74, the pressure member 76 is provided with a slot 78 that extends from a generally central portion of the pressure member 76 radially outward, defining a gap in the peripheral edge 80 of the pressure member 76. The pressure member 76 of this embodiment is thus of a generally U-shaped configuration. The slot 78 is adapted to be aligned with a portion of a blood vessel of the patient proximate a site intended, for example, for drawing blood or the placement of an IV catheter.

The pressure member 76 is a relatively thin, generally flat disk that has a skin engaging surface on its underside formed by the ends of a plurality of projections 82. In addition, the peripheral edge 80 of the pressure member 76 has been configured so as to have at least one noncircular section to facilitate handling of the pressure member. Thus, the peripheral edge 80 is scalloped, giving the apparatus a generally cloverleaf shape. The peripheral edge 80 has also been formed of a thickness greater than the thickness of the more central portions of the pressure member 76, thereby defining a raised lip about the periphery of the pressure member.

Thus, in accordance with various embodiments of the method of the invention, the pain associated with penetration of the skin of a patient at a site with a needle or surgical instrument is reduced by urging a skin engaging surface of a pressure member against the skin of a patient at the site. The pressure applied by the skin engaging surface stimulates the large diameter afferent sensory nerve fibers in the skin proximate the site, at least partially blocking pain signals from the small diameter afferent pain nerve fibers in the skin proximate the site.

The peripheral edge of the apparatus is readily gripped in the hand of a user. The apparatus is then manipulated so as to urge the skin engaging surface of the pressure member against the skin of the patient proximate the injection or surgical site. Where an aperture is provided in the pressure member, the aperture is aligned with the desired injection or surgical site. Where a slot is provided in the pressure member, the slot may, as an example, be aligned with a desired blood vessel.

When the skin engaging surface of the pressure member is urged against the skin of the patient with sufficient force, the skin is depressed and the pressure sensory nerves located in the skin proximate the site are stimulated. Nerve impulses from these fibers flood the dorsal horn gate and inhibit the transmission of pain nerve impulses from the same area. The pressure is applied to the skin through the skin engaging surface of the pressure member in such a manner that the nerve impulses from the large fiber nerves reach the dorsal horn gate prior to the nerve impulses from the small fiber nerves stimulated by penetration of the needle or surgical instrument.

This generally means that the skin engaging surface contacts the skin proximate the site at a time just slightly before the needle or surgical instrument contacts the skin at the site. The pressure exerted against the skin by the skin engaging surface of the pressure member may be maintained until the injection or minor surgical procedure has been completed. If the pressure is applied too far in advance of the injection or surgical procedure, the large diameter afferent sensory nerve fibers will have a chance to repolarize and stop sending signals down the afferent pathway. This would allow the gate to open in response to pain nerve fiber impulses and again allow the patient to perceive the painful stimulus.

The invention thus provides a method of reducing or eliminating the pain from injections or simple surgical procedures by the local application of pressure circumferential to the injection or surgical site, thus blocking afferent pain fiber transmission by application of gate theory. Various embodiments of an apparatus of the invention produces non-noxious mechanical pressure in the local area of the injection or surgical site in order to stimulate large diameter afferent sensory nerve fibers to block the co-incident transmission of pain fiber impulses through practical application of gate theory. In this manner, the pain from injections, such as those associated with immunizations or insulin shots, and minor surgical procedures might be mitigated significantly.

Figure 13:
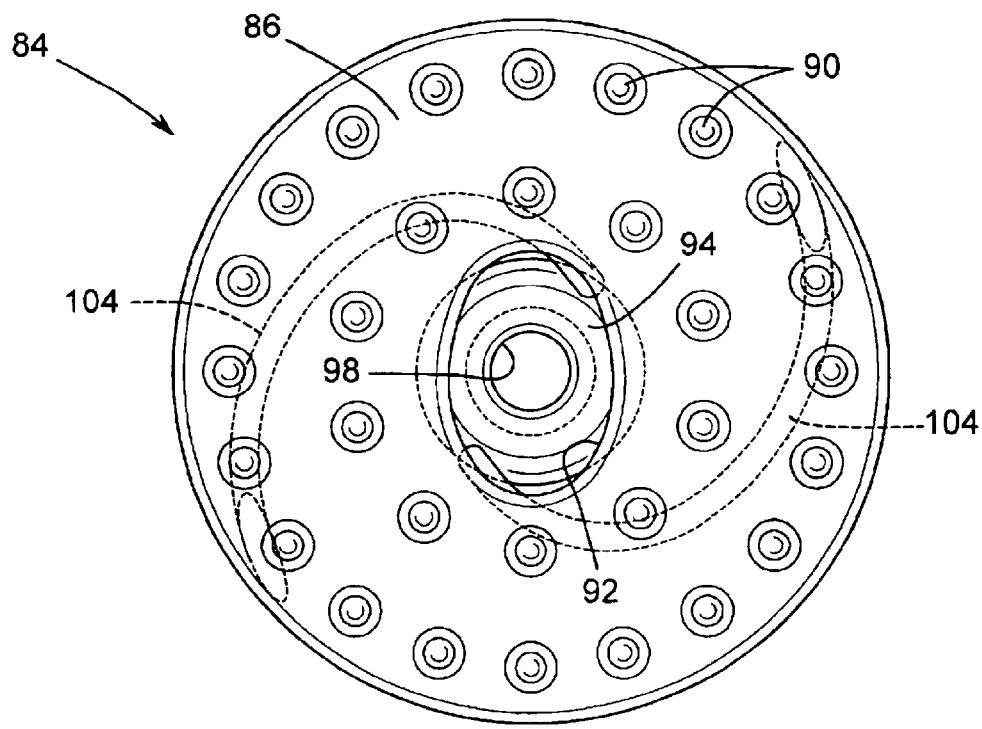
FIG. 13 is a bottom view of a ninth embodiment of an apparatus in accordance with the invention with certain features shown in hidden lines.
Figure 14:
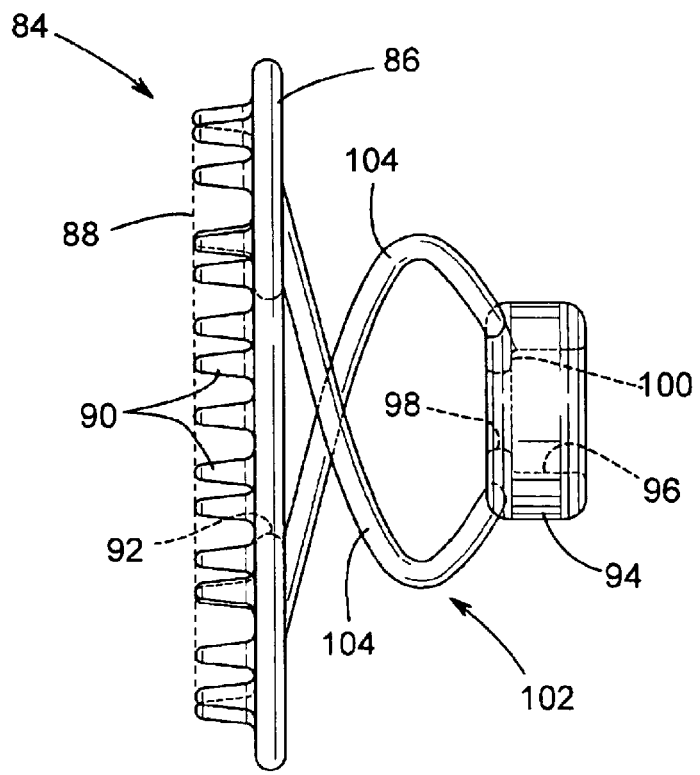
FIG. 14 is a side view of the apparatus shown in FIG. 13 with certain features shown in hidden lines.

A further apparatus 84 in accordance with the invention is illustrated in FIGS. 13 and 14. The apparatus 84 is adapted especially for use with a hypodermic syringe and may, for example, be especially useful for the administration of routine insulin injections. The apparatus 84 is comprised of a body member or pressure member 86 having a skin engaging surface 88 adapted to be pressed against the skin of a patient at a site to stimulate the large diameter afferent sensory nerve fibers in the skin proximate the injection site and at least partially block pain signals from the small diameter afferent pain nerve fibers in the skin proximate the site.

As illustrated, the skin engaging surface 88 is formed by the ends of a plurality of projections 90 that are spaced about and extend from the underside of the pressure member 86. The projections 88 in this embodiment are shown as being substantially conical in shape with rounded ends. A number of shapes and configurations will provide adequate sensory and pressure nerve stimulation and thus will be efficacious in this application and may be substituted for the shape shown.

An aperture 92 is provided in the pressure member 86 to allow for the introduction of the needle of a hypodermic syringe (not shown) once the apparatus has been applied to the skin. As shown in FIGS. 13 and 14, the aperture 92 is generally centrally located and is generally circular in shape, so that the projections 90 substantially surround the aperture 92.

The apparatus 84 further includes a syringe retainer 94 adapted to be secured to a syringe. The syringe retainer 94 is annular in shape, being provided with a central bore 96 adapted to receive the barrel of the syringe in a friction fit. The bore 96 includes a reduced diameter lower portion 98 that allows for the passage of the needle, while defining a step 100 that abuts a portion of the syringe, thereby preventing axial movement of the syringe relative to the syringe retainer 94 in the direction of the pressure member 86.

The syringe retainer 94 is resiliently connected to the pressure member 86 by one or more resilient members, such as the spring 102. It will be understood that other types of resilient, compressible structures may function as well to provide the necessary tension for the device and may be substituted for the helical spring mechanism shown in the drawings. The spring 102 as shown has two helical segments 104. The spring 102 is adapted to be compressed under the force used to administer an injection to a patient, allowing the pressure member 86 and the syringe retainer 94 to move towards each other in a linear fashion so that the needle penetrates the skin at the injection site. The spring 102 or other resilient, compressible structure provides enough resistance to movement of the pressure member 86 relative to the syringe retainer 94 that, when the pressure member 86 contacts the skin, the projections 90 depress the skin with sufficient force to stimulate the large diameter afferent sensory nerve fibers.

The apparatus 84 of the invention may be formed of any suitable material or combination of materials. Polymeric materials such as polyethylene are especially suitable. Multiple portions or the entire apparatus 84 may be molded as an integral part from a polymeric material such as polyethylene.

In accordance with the provisions of the patent statutes, the invention has been described in what is considered to represent its preferred embodiments. However, it should be noted that the invention can be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A method for reducing the pain associated with penetration of the skin of a patient at a site with a needle or surgical instrument, comprising providing a pressure member having a generally flat disk shape and being relatively broad in relation to the thickness of the pressure member, the pressure member having a skin engaging surface comprised of a plurality of projections extending from said pressure member, wherein the disc completely encircles the penetration site and urging the skin engaging surface of the pressure member against the skin of a patient proximate the site, to thereby depress the skin with sufficient force to stimulate the large diameter afferent sensory nerve fibers in the skin proximate the site and at least partially block pain signals from the small diameter afferent pain nerve fibers in the skin proximate the site.

2. The method of claim 1, wherein the skin engaging surface of the pressure member is urged against the skin proximate the site shortly prior to or at the same time as that the needle or surgical instrument contacts the skin at the site.

3. The method of claim 1, wherein the pressure member is comprised of a material that is flexible enough to substantially conform to the contours of the skin in the vicinity of the site as the pressure member is urged against the skin.

4. The method of claim 1, wherein the pressure member is comprised of a flexible, polymeric material.

5. The method of claim 1, wherein the pressure member is comprised of a rigid material.

6. The method of claim 5, wherein the pressure member is comprised of metal.

7. The method of claim 1, wherein the skin engaging surface of the pressure member extends about an aperture formed in the pressure member, and the needle or surgical instrument is introduced through the aperture to contact the skin at the site.

8. The method of claim 1, wherein the ends of the projections are blunt relative to the end of the needle or surgical instrument being employed.

9. The method of claim 1, wherein the perimeter of the pressure member is formed with at least one noncircular section to facilitate handling of the pressure member.

10. The method of claim 9, wherein the perimeter of the pressure member defines a generally cloverleaf shape.

11. The method of claim 1, wherein when the skin engaging surface of the pressure member is urged against the skin proximate the site, the skin engaging surface substantially conforms to the contours of the skin proximate the site.

12. The method of claim 1, wherein the perimeter of the pressure member defines a circular shape.

13. The method of claim 1, wherein the perimeter of the pressure member defines a generally oval shape.

* * * * *